United States Patent [19]

Kende et al.

[11] 4,391,982
[45] Jul. 5, 1983

[54] INTERMEDIATES FOR THE PRODUCTION OF PICROPODOPHYLLIN AND RELATED COMPOUNDS AND PROCESSES FOR THE PREPARATION AND USE THEREOF

[75] Inventors: Andrew S. Kende, Pittsford, N.Y.; Dennis P. Curran, Madison, Wis.; Margaret L. King, Rochester; Neil A. Feldstein, Westbury, both of N.Y.

[73] Assignee: The University of Rochester, Rochester, N.Y.

[21] Appl. No.: 247,279

[22] Filed: Mar. 25, 1981

Related U.S. Application Data

[62] Division of Ser. No. 127,436, Mar. 5, 1980, Pat. No. 4,294,763.

[51] Int. Cl.$^3$ ................. C07D 317/44; C07C 69/76
[52] U.S. Cl. ..................................... 549/433; 560/56;
564/158; 568/312; 568/327
[58] Field of Search .............. 260/340.5 DP, 340.5 R,
260/465 H; 560/56; 562/466; 549/433;
564/158; 568/312, 327

[56] References Cited

U.S. PATENT DOCUMENTS 2,507,473  5/1950  Koelsch ..................... 260/465 H
2,658,910 11/1953  Johnson et al. ................ 560/56

OTHER PUBLICATIONS

Gensler et al, Journ. Amer. Chem. Society, vol. 82, pp. 1714–1727, (1960).

*Primary Examiner*—Ethel G. Love
*Attorney, Agent, or Firm*—Roylance, Abrams, Berdo & Farley

[57] ABSTRACT

The present invention provides compounds having the structure:

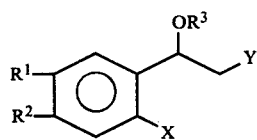

VI wherein $R^1$ represents alkoxy or aralkoxy, $R^2$ represents hydrogen, alkoxy, aralkoxy, alkyl, aralkyl, or $R^1$ and $R^2$ taken together represent the group —O—CH$_2$—O—, $R^3$ represents hydrogen, alkyl, aralkyl, acyl or a protecting group, Y represents Cl, Br, I or a leaving group; and X represents Cl, Br or I.

The present invention also provides a process for preparation of compounds VI in a single step wherein X and Y are the same and represent Cl, Br, or I, and $R^3$ is as previously defined except that in this instance, it does not represent a protecting group.

According to another aspect of the present invention there are provided compounds VII-a and VII-b having the structure:

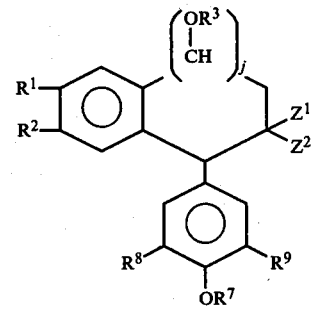

VII-a; j = 1
VII-b; j = 0 wherein $R^1$, $R^2$ and $R^3$ are as previously defined, j is an integer having a value of 0 or 1, $Z^1$ represents a non-reacting electron withdrawing group, and $Z^2$ represents a non-reacting electron withdrawing group or hydrogen, $R^8$ and $R^9$ are the same or different and represent hydrogen, alkyl, aralkyl, alkoxy, or aralkoxy, and $R^7$ represents hydrogen, alkyl, aralkyl or acyl. Compounds VII-a may be prepared from compounds VI through the use of the process of "insertion-cyclization" which is provided by another aspect of the present invention.

According to a further aspect of the present invention, compounds VII-a are converted into tetralone III-a shown below:

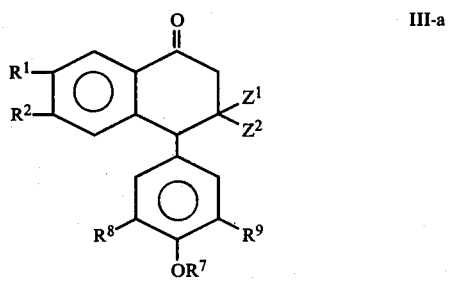

III-a wherein $R^1$, $R^2$, $R^3$, $Z^1$, $Z^2$, $R^7$, $R^8$ and $R^9$ are as previously defined. Certain of these compounds can, in turn, be readily converted into picropodophyllin and picrosikkimotoxin. The latter can be converted into known antineoplastic agents by known procedures.

12 Claims, No Drawings

INTERMEDIATES FOR THE PRODUCTION OF PICROPODOPHYLLIN AND RELATED COMPOUNDS AND PROCESSES FOR THE PREPARATION AND USE THEREOF

This is a division of application Ser. No. 127,436, filed Mar. 5, 1980, now U.S. Pat. No. 4,294,763.

BACKGROUND OF THE INVENTION

1. Field Of The Invention

The present invention is directed to intermediates which can be converted into podophyllotoxin and related compounds, which are known antineoplastic agents. Additionally, the present invention provides processes for the preparation of such intermediates, and processes for the conversion of the intermediates into known intermediates which are readily converted into podophyllotoxin and related compounds.

2. Description of the Prior Art

Podophyllotoxin (I), a known lignan lactone isolated from several species of Podophyllum, is a potent cytotoxic agent. Numerous other related compounds having the characteristic aryltetralin ring structure, either naturally occurring or derived from some naturally occurring compounds are known. Some of these compounds possess antineoplastic activity while others are useful for conversion to compounds having such activity. Podophyllotoxin has the structure shown below:

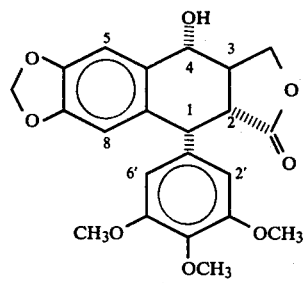

Podophyllotoxin

Podophyllotoxin has also been prepared synthetically. The synthesis involves the production of picropodophyllin (II), shown below:

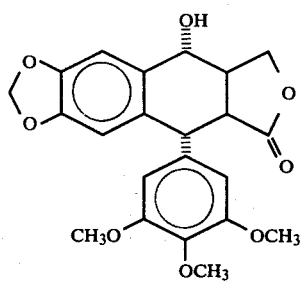

Picropodophyllin

Picropodophyllin is the cis-lactone isomer of podophyllotoxin (I), and can be epimerized into podophyllotoxin (I) according to the procedure of Gensler et al, described in J. Org. Chem., 31, 404–8 (1966). The epimerization is accomplished by preparing the O-tetrahydropyranyl derivative of picropodophyllin, converting it to the sodium enolate by treatment with triphenylmethylsodium, and quenching the enolate with excess acetic acid.

In J. Am. Chem. Soc., 82, 1714–1727 (1960), Gensler et al report the total synthesis of picropodophyllin (II) by a lengthy procedure involving 14 steps and a low overall yield.

More recently, in U.S. Pat. No. 4,122,092 to Andrew S. Kende and Peter S. Rutledge, there has been described a simpler, more direct route for the production of picropodophyllin (II) involving, as an intermediate, a tetralone of formula III, (their XV), shown below:

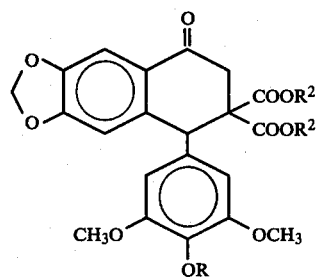

wherein $R^2$ is alkyl and R is methyl or hydrogen. Compound III is produced by a four-step procedure utilizing 2-(3,4-methylenedioxyphenyl)ethyl mesylate as a starting material, wherein the immediate precursor to the tetralone III is the corresponding tetralin. However, oxidation of the tetralin to the tetralone III cannot readily be achieved on a larger than 0.2 g. scale and thus presents a volumetric limitation to the synthesis. Conversion of the tetralone III to picropodophyllin (II) is thereafter readily accomplished by the four-step procedure disclosed in the above-cited Kende et al patent.

U.S. Pat. No. 3,524,844 to Keller-Juslen et al. discloses 4′-demethylepipodophyllotoxin-β-D-(substituted) glucosides of the formula:

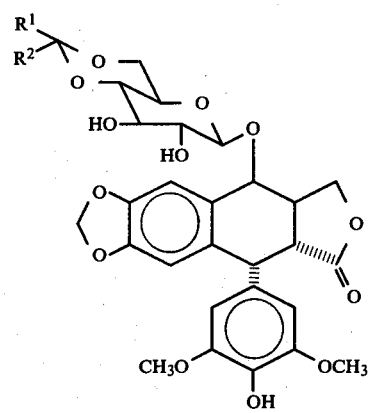

wherein, inter alia, $R^1$ is hydrogen and $R^2$ is an alkyl or a 2-thienyl moiety. These compounds are prepared from 4′-demethylepipodophyllotoxin V shown below:

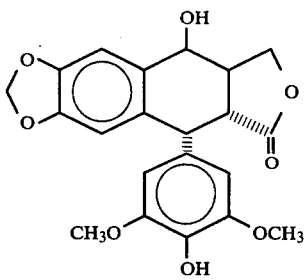

which, in turn, is prepared from podophyllotoxin. Both of the latter conversions are described in U.S. Pat. No. 3,524,844. The 4'-demethylepidophyllotoxin-$\beta$-D-(substituted)-glucosides are antineoplastic agents.

SUMMARY OF THE DISCLOSURE

The present invention provides compounds having the structure:

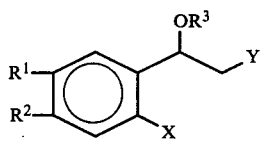

wherein $R^1$ represents alkoxy or aralkoxy, $R^2$ represents hydrogen, alkoxy, aralkoxy, alkyl, aralkyl, or $R^1$ and $R^2$ taken together represent the group —O—CH$_2$—O—, $R^3$ represents hydrogen, alkyl, aralkyl, acyl or a protecting group, Y represents Cl, Br, I or a leaving group; and X represents Cl, Br or I.

The present invention also provides a process for preparation of compounds VI in a single step wherein X and Y are the same and represent Cl, Br, or I, and $R^3$ is previously defined, except that in this instance, it does not represent a protecting group.

According to another aspect of the present invention there are provided compounds VII-a and VII-b having the structure:

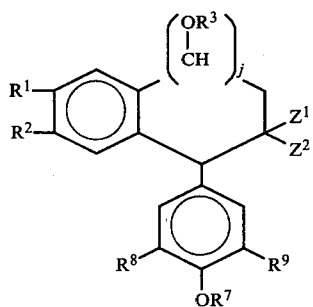

VII-a; j = 1
VII-b; j = 0 wherein $R^1$, $R^2$ and $R^3$ are as previously defined, j is an integer having a value of 0 or 1, $Z^1$ represents a nonreacting electron withdrawing group, and $Z^2$ represents a non-reacting electron withdrawing group or hydrogen, $R^8$ and $R^9$ are the same or different and represent hydrogen, alkyl, aralkyl, alkoxy, or aralkoxy, and $R^7$ represents hydrogen, alkyl, aralkyl or acyl. Compounds VII-a may be prepared from compounds VI through the use of the process of "insertion-cyclization" which is provided by another aspect of the present invention.

According to a further aspect of the present invention, compounds VII-a are converted into tetralone III-a shown below:

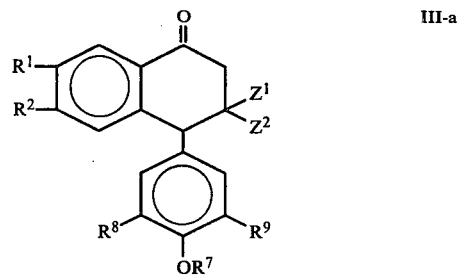

wherein $R^1$, $R^2$, $R^3$, $Z^1$, $Z^2$, $R^7$, $R^8$ and $R^9$ are as previously defined. Certain of these compounds, i.e., when $Z^1$ and $Z^2$ are each COO(lower alkyl), $R^8$ and $R^9$ are each methoxy and $R^7$ is methyl, hereinafter tetralone III-b, can, in turn, be readily converted into picropodophyllin (II) and picrosikkimotoxin (VIII), shown below:

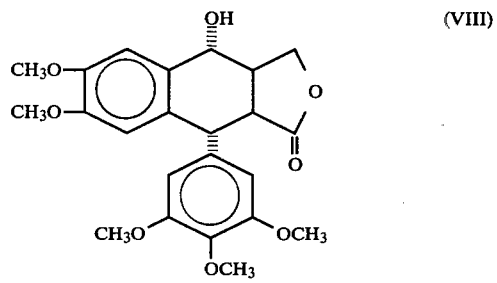

Picrosikkimotoxin through the procedures disclosed in U.S. Pat. No. 4,122,092 to Kende et al, at column 7, line 36 through column 8, line 17.

The latter, i.e., compounds II and VIII, are readily converted into antineoplastic agents podophyllotoxin (I) and sikkimotoxin (IX), shown below:

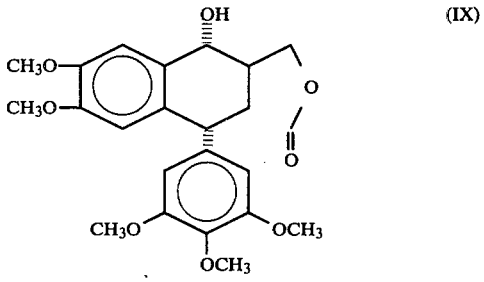

Sikkimotoxin through the Gensler enolate quenching procedure previously described. Podophyllotoxin is converted into the antineoplastic agents, 4'-demethylepipodophyllotoxin-$\beta$-D-(substituted)glucosides (IV), by the procedure of U.S. Pat. No. 3,524,844.

Accordingly, the present invention provides a simple, straightforward procedure for preparing known antineoplastic agents. Use of the intermediates and processes of the present invention avoids the volumetrically limiting tetralin to tetralone oxidation step of the prior art. Additionally, the intermediates of the present invention can be readily prepared from less complex, and often commercially available starting materials such as piperonal.

PREFERRED EMBODIMENTS OF THE PRESENT INVENTION

According to one aspect of the present invention there are provided compounds of the formula:

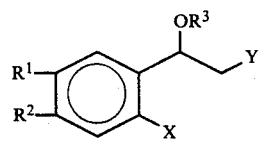
VI wherein $R^1$ represents alkoxy or aralkoxy, $R^2$ represents hydrogen, alkoxy, aralkoxy, alkyl or aralkyl, or $R^1$ and $R^2$ taken together represent the group —O—CH$_2$—O—, $R^3$ represents hydrogen, alkyl, aralkyl, acyl, or a conventional protecting group which is stable to anhydrous bases such as alkyl lithium. Protecting groups which are stable to anhydrous base are well known to those skilled in the art and include moieties such as tetrahydropyranyl, trialkyl silyl, methoxymethyl, α-ethoxyethyl and the like. Other suitable protecting groups are disclosed in: PROTECTIVE GROUPS IN ORGANIC CHEMISTRY, McOmie (Plenum Press, 1973), Chapter 3, which is hereby incorporated by reference. Y represents Cl, Br, I or a conventional leaving group. Suitable leaving groups are well known to those skilled in the art and include, for example, tosylate, brosylate, nosylate, mesylate, triflate, nonaflate, tresylate, etc.; and X represents Cl, Br or I, preferably Br or I.

In a preferred embodiment of the present invention, there are provided compounds of the formula:

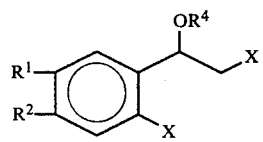
VI-a wherein $R^1$, $R^2$ and X are as previously defined, and $R^4$ is the same as $R^3$ except that $R^4$ cannot be a protecting group. Thus $R^4$ represents hydrogen, alkyl, aralkyl or acyl. It is also preferred that X represent Br. Additionally, it is preferred that $R^4$ represent lower alkyl, i.e., a group containing 1 to 6 carbon atoms, and most preferably methyl. Furthermore, it is preferred that $R^1$ and $R^2$, both represent methoxy, or taken together, represent the group —O—CH$_2$—O—. Most preferably $R^1$ and $R^2$ taken together represent the group —O—CH$_2$—O—.

Preparation of compounds VI may be accomplished in any suitable manner. Preferably, compounds VI-a are prepared according to another aspect of the present invention in a single step from the corresponding (substituted)styrene by treating the styrene with any source of electrophilic bromine, iodine, or chlorine, together with $R^4$OH wherein $R^4$ is as previously defined, i.e., hydrogen, alkyl, aralkyl or acyl. The preparation of compounds VI-a is shown below:

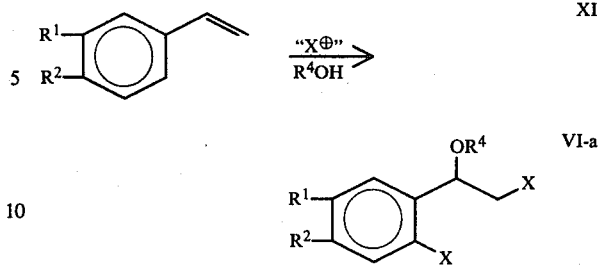

Sources of electrophilic halogens include: in the case of bromine, elemental bromine, and N-bromoamides such as N-bromosuccinimide or N-bromoacetamide; in the case of chlorine, elemental chlorine, and N-chloroamides; and in the case of iodine, a solution of iodine with an oxidizing agent such as HgO, HIO$_3$, etc.

When $R^4$OH is an alcohol, i.e., when $R^4$ is alkyl or aralkyl, the alcohol is also the solvent. When $R^4$OH is water or a carboxylic acid, a co-solvent such as acetone, dimethylsulfoxide, or dioxane, preferably acetone, should be utilized. Additionally when $R^4$OH is water or a carboxylic acid, an alkali salt of a carboxylic acid is preferably utilized. Thus, for instance, when $R^4$OH is water or acetic acid, the reaction is preferably conducted in the presence of sodium acetate. When the acid is other than acetic acid, the corresponding acid salt is preferably utilized.

The above reaction is conveniently carried out at a temperature of between about $-20°$ C. and about $+30°$ C., preferably at about room temperature, i.e., 23° C. In a preferred embodiment, the source of electrophilic halogen will comprise elemental bromine and $R^4$OH will comprise a (lower)alkyl, i.e., 1-6 carbon atoms, alcohol such as methanol, ethanol, isopropanol, t-butyl alcohol, etc, most preferably methanol.

If desired, compounds VI may be provided by a stepwise procedure by, for instance, halogenating a (substituted) benzaldehyde to provide the ortho-halo(substituted)benzaldehyde, converting the o-halo(substituted)benzaldehyde to the corresponding styrene, and treating the styrene with a source of electrophilic halogen, which may be the same or different halogen as the ring halogen, together with $R^4$OH. Thus, for instance, 3,4-methylenedioxybenzaldehyde (piperonal) may be treated with iodine and a silver salt to provide 3,4-methylenedioxy-6-iodobenzaldehyde. The latter is converted to the corresponding styrene by treatment with (methyl)triphenylphosphonium bromide and a suitable base such as potassium carbonate or n-butyl lithium, according to the Wittig reaction to provide the ortho-iodo(substituted)styrene. The styrene is treated with bromine or chlorine in a simple alcohol, i.e., methanol, ethanol, etc., to provide compound VI wherein Y is bromine or chlorine and X is iodine. Compounds VI or VI-a may, if desired, be treated to convert the side chain halogen to another leaving group, and/or to convert $R^3$ or $R^4$ to any of the previously enumerated protecting groups by means known to those skilled in the art.

According to another aspect of the present invention, there are provided compounds VII-a and VII-b, shown below:

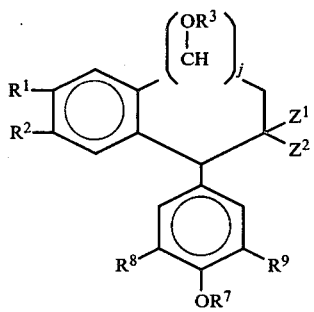

VII-a; j = 1
VII-b; j = 0 wherein $R^1$, $R^2$ and $R^3$ are as previously defined, j is an integer, having a value of 0 or 1, $Z^1$ represents a conventional non-reacting electron withdrawing group. Non-reacting electron withdrawing groups are well known to those skilled in the art and include, for example, COO(alkyl), COO(aryl), COO(aralkyl); substituted ketones such as CO(alkyl), CO(aryl) and CO(aralkyl) and amides such as, $CONH_2$, etc. $Z^2$ represents a conventional non-reacting electron withdrawing group or hydrogen. Preferred electron withdrawing groups are those which can readily be converted to a carboxyl group. It is also preferred that both $Z^1$ and $Z^2$ represent electron withdrawing groups. $R^8$ and $R^9$ are the same or different and represent hydrogen, alkyl, aralkyl, alkoxy, aralkoxy, or acyl and $R^7$ represents hydrogen, alkyl, aralkyl or acyl.

In a preferred embodiment, $Z^1$ represents $COOR^5$ and $Z^2$ represents $COOR^6$, wherein $R^5$ and $R^6$ are the same or different and represent alkyl, or aralkyl, and j represents the integer 1. Preferably $R^5$ and $R^6$ are the same and represent lower alkyl, most preferably, ethyl. Additionally, it is preferred that $R^3$ represent lower alkyl and that $R^1$ and $R^2$ represent methoxy or, taken together, represent the group —O—$CH_2$—O—. $R^8$ and $R^9$ are preferably lower alkoxy, most preferably methoxy while $R^7$ is preferably lower alkyl or aralkyl, most preferably methyl or benzyl.

Compounds VII-a and VII-b can be prepared from compounds VI and VI-b (shown below) through the process of "insertion-cyclization", which is provided in accordance with another aspect of the present invention. The insertion-cyclization reaction, as as utilized herein, is shown below:

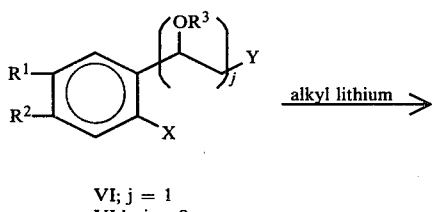

VI; j = 1
VI-b; j = 0

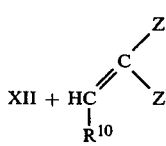

XII

XII +

XIII            XIV wherein $R^1$, $R^2$, $R^3$, $Z^1$, $Z^2$, Y, X and j are as previously defined; $R^{10}$ represents hydrogen, alkyl, aryl, substituted aryl, or aralkyl.

The reaction proceeds most readily when X represents I or Br. The alkyl lithium utilized may be any primary, secondary or tertiary alkyl lithium. When X represent I, a primary alkyl lithium is preferred because of cost. When X represents Br, it is preferred that the alkyl lithium utilized be a secondary or tertiary alkyl lithium and when X represents Cl, it is preferred that the alkyl lithium be a tertiary alkyl lithium. Any inert solvent which is liquid at reaction temperatures may be utilized. A preferred solvent constitutes a mixture of diethyl ether and tetrahydrofuran.

The insertion-cyclization reaction sequence shown above should be initiated at a temperature of less than $-40°$ C., preferably at a temperature of less than $-78°$ C., most preferably at a temperature of about $-100°$ C. The reaction is initiated by adding the alkyl lithium to compound VI or VI-b to provide lithium-halogen exchange thus forming compound XII as an unisolated intermediate. The exchange proceeds most readily when t-butyllithium is used and has been found to be completed within ten minutes when the ring halogen, i.e., X, is Br or I. Completeness of the exchange can readily be determined by NMR examination of an aliquot the reaction mixture after quenching with water.

Upon completion of the exchange, compound XIII is slowly added to the reaction mixture followed by agitation for a short period of time, i.e., up to about an hour. The mixture is thereafter slowly warmed to a temperature of between about 0° C. and about 120° C., preferably between about 40° C. and 90° C., and stirred or refluxed to complete the ring closure. It has been found that ring closure proceeds slowly at lower temperatures, e.g., several days at about 20° C., and rapidly at higher temperatures, e.g., an hour at 85° C.

In order to reflux the mixture at the preferred elevated temperatures, it may be necessary to remove the lower boiling solvent and replace the same with a higher boiling inert solvent, such as an ether or benzene. A preferred inert solvent is 1,2-dimethoxyethane which has a boiling point of 83° C. Completion of ring closure can be determined by NMR examination of the reaction product.

Compounds XIII are readily available via the Knoevenagel condensation of a di(electron withdrawing group)methane with an aldehyde. The Knoevenagel reaction is well known and forms no part of the present invention. A detailed discussion of the reaction may be found in: ADVANCED ORGANIC CHEMISTRY, 2nd Ed., March (McGraw-Hill, 1977) pages 854–859, which pages are hereby incorporated by reference.

It is preferred that $R^{10}$ represent the radical:

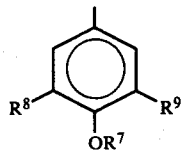

wherein $R^7$, $R^8$ and $R^9$ are as previously defined. Additionally, it is preferred that $Z^1$ represent $COOR^5$ and $Z^2$ represent $COOR^6$ wherein $R^5$ and $R^6$ are as previously defined.

Most preferably, the reaction is carried out wherein j represents the integer 1 and $R^5$ and $R^6$ represent the same or different lower alkyl, most preferably ethyl. Additionally, it is preferred that $R^3$ represent lower alkyl and that $R^1$ and $R^2$ each represent methoxy or, taken together, represent —O—CH$_2$—O—. $R^8$ and $R^9$ are preferably lower alkoxy, most preferably methoxy, while $R^7$ is preferably lower alkyl or aralkyl, most preferably methyl or benzyl.

According to another aspect of the present invention, the novel intermediates of the present invention, compounds VII-a, are converted to the corresponding tetralone III-a as shown below:

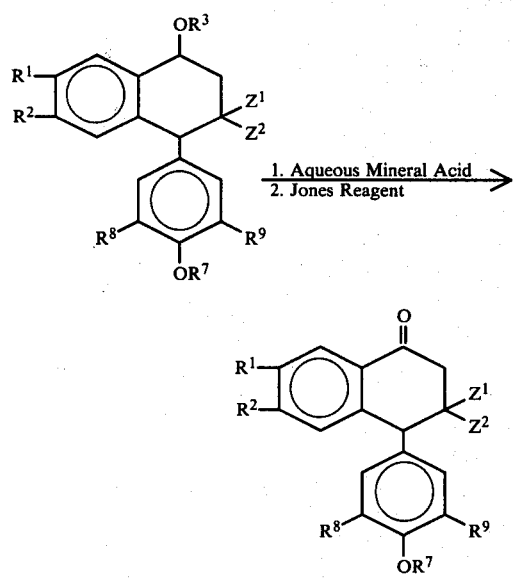

wherein $R^1$, $R^2$, $R^3$, $R^7$, $R^8$, $R^9$, $Z^1$, $Z^2$ are as previously defined. Thus, compounds VII-a are treated with an aqueous mineral acid such as H$_2$SO$_4$, HCl, HBr, etc., preferably HCl, to effect hydrolysis and to thus provide the corresponding alcohol at C-4, and the alcohol is oxidized to the ketone III-a, by the Jones oxidation.

The hydrolysis is conducted at a temperature of about −20° C. to about 40° C., preferably about 0° C., in any polar solvent, preferably acetone. The hydrolysis is continued until disappearance of the starting material at which point Jones reagent may be added. The Jones Oxidation and Jones reagent are well known to those skilled in the art. The same are discussed in Bowden et al., J. Chem. Soc. 39 (1946) and Bowers et al., J. Chem. Soc. 2548 (1953). Upon completion of the Jones oxidation, the reaction is quenched, e.g., with methanol, to provide the tetralone III-a.

As indicated earlier, the previously described tetralones III-b can readily be converted into picropodophyllin (II) and picrosikkimotoxin (VIII). If tetralone III-a is in a form other than that of tetralone III-b, it is converted into tetralone III-b by means known to those skilled in the art. Thereafter, tetralone III-b can be converted to the above-stated compounds by the process disclosed in U.S. Pat. No. 4,122,092 to Kende et al which is hereby incorporated by reference.

With regard to previous references to lower alkyl and lower alkoxy groups, for the purposes of the present disclosure the term, lower alkyl, is intended to mean a straight or branched chain alkyl moiety containing 1 to 6 carbon atoms and the term, lower alkoxy, is intended to mean a straight or branched chain alkoxy moiety having 1 to 6 carbon atoms.

A particularly preferred reaction sequence conducted in accordance with the various aspects of the present invention is shown below:

A. Preparation of Starting Material:

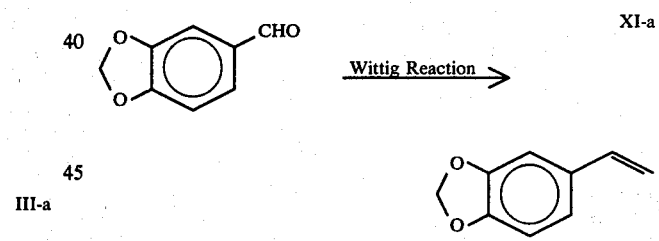

(B) Preparations And Intermediates Of Present Invention:

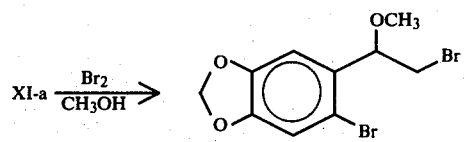

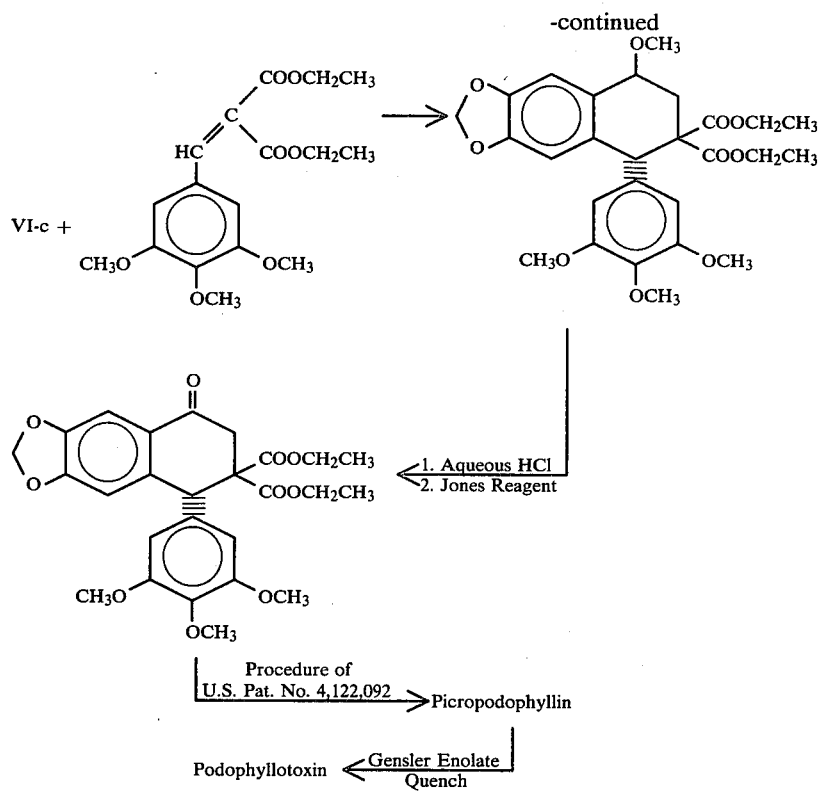

The following examples serve to illustrate the intermediates and processes of the present invention.

EXAMPLE 1

2-Methoxy-2(6-bromo-3,4-methylenedioxyphenyl)-1-bromoethane (VI-a; where X=Br, $R^1$ and $R^2$=O—$CH_2$—O, $R^4$=$CH_3$)

(a) Preparation of Starting Material: 3,4-Methylenedioxystyrene

To a stirred suspension of (methyl)triphenylphosphonium bromide (17.1 g, 48 mmol) and potassium carbonate (6.63 g, 48 mmol) in THF (200 ml) were added piperonal (6.0 g, 40 mmol) and 18-crown-6 (120 mg, 0.46 mmol). The mixture was heated to reflux under nitrogen and refluxed for 36 hours. The reaction mixture was cooled to room temperature, filtered and the filtrate evaporated to dryness at 15° C. The resulting solid was stirred in 100 ml cold diethylether to dissolve the desired product, then filtered to remove inorganic salts, and the filtrate evaporated at 15° C. This process was repeated a second time. The product was filtered through 60 g basic alumina (pentane/ether, 24/1) and the solvent removed as before to give 5.36 g (89%) of the liquid styrene. NMR ($CDCl_3$) δ 6.89 (1H, singlet), 6.70–6.74 (2H, 2 overlapping singlets), 6.43–6.7 (1H, partially obscured doublet), 5.84(2H, singlet), 5.50(1H, doublet), 5.06(1H, doublet).

(b) Preparation of Title Compound:

Bromine (3.15 ml, 61.4 mmol) was added dropwise to a stirred solution of 3,4-methylenedioxystyrene (3.0 g, 20.0 mmol) in dry methanol (60 ml) under nitrogen at 0° C. The resulting solution was stirred at 0° C. for 15 minutes, then at room temperature for 36 hours, at which point a white precipitate had appeared, and the reaction was complete by TLC (ether/cyclohexane,1/1). The reaction mixture was cooled to 0° C. and filtered, and the product was washed with cold methanol, yielding 4.07 g. The mother liquors were evaporated, and the residue poured into water containing several spatula tips of sodium bisulfite. This was extracted with methylene chloride three times, and the combined extracts were washed with water, saturated sodium bicarbonate and saturated sodium chloride, filtered through sodium sulfate, and evaporated. The resulting off-white solid was recrystallized twice from methanol, to give an additional 0.67 g of the title compound. Total yield: 5.34 g (79%); m.p. 87°–88.5° C., NMR ($CDCl_3$) δ 6.92 (1H, singlet), 6.88 (1H, singlet), 5.94 (2H, singlet), 4.68 (1H, doublet), 3.44 (2H, multiplet), 3.29(3H, singlet); Mass Spec. 340,338,336 (M+).

EXAMPLE 2

4-Methoxy-2,2-dicarbethoxy-6,7-methylenedioxy-1-(3',4',5'-trimethoxyphenyl)tetralin; (VII-a; where $R^1$ and $R^2$=O—$CH_2$—O, $R^3$=$CH_3$, $Z^1$, $Z^2$=$COOC_2H_5$, $R^7$=$CH_3$, $R^8$, $R^9$=$OCH_3$)

To a solution of the methoxydibromide prepared in Example 1 (490 mg., 1.45 mmol) in ether (8 ml) at −100° C. (ether/liquid nitrogen) under nitrogen was added t-butyllithium (0.98 ml, 1.52 mmol, 1.55 M in pentane) dropwise via syringe. The reaction mixture was stirred for 30 minutes at −100° C., and then diethyl(3,4,5-trimethoxyphenyl)methylenemalonate (490 mg, 1.45 mmol) [prepared by the method of Papadakis et al, J. Org. Chem, 21, 593 (1956)] in tetrahydrofuran (1.5 ml) was added slowly via syringe. The reaction was maintained at −100° C. for 1 hour and then allowed to come slowly to room temperature and stirred for 16 hours. The ether and THF were removed with a nitrogen stream and 1,2-dimethoxyethane (8 ml) was distilled into the reaction vessel. The solution was refluxed for 1 hour under nitrogen, poured into dilute ammonium chloride, and extracted with methylene chloride. The organic layer was washed with water and saturated sodium chloride, dried over sodium sulfate, and concentrated under reduced pressure to give 730 mg of crude title product as a 3/2 mixture of diastereomers by NMR. A small portion (78 mg) was purified by separative thin layer chromatography (ether/cyclohexane, 1/1) to give 27 mg of the less polar diastereomer; NMR (CDCl$_3$) δ 6,87 (1H, singlet), 6.37 (1H, singlet), 6.25 (2H, singlet), 5.84 (2H,singlet), 4.74 (1H, singlet), 4.16 (5H, multiplet), 3.78 (3H, singlet), 3.73 (6H, singlet), 3.58 (3H, singlet), 2.3–2.7 (2H, multiplet), 1.20 (6H, two overlapping triplets); Mass Spec., 516 (M+); and 39 mg of the more polar diastereomer; NMR (CDCl$_3$)δ6.77(1H, singlet), 6.46 (1H, singlet), 6.17 (2H, singlet), 5.90(2H, doublet), 4.87(1H, singlet), 4.2(5H, multiplet), 3.84(3H, singlet), 3.81(6H, singlet), 3.54(3H, singlet), 2.90(1H, broad doublet), 2.52(1H, doublet), 1.20(6H, two overlapping triplets); Mass Spec. 516 (M+). Total yield: 117 mg (85%). The crude mixture was used directly for the oxidation (Example 5).

EXAMPLE 3

4-Methoxy-2,2-dicarbethoxy-1-(3',5'-dimethoxy-4'-benzyloxyphenyl)-6,7-methylenedioxytetralin (VII-a; where R$^1$ and R$^2$=O—CH$_2$—O, R$^3$=CH$_3$, Z$^1$,Z$^2$=COOC$_2$H$_5$, R$^7$=C$_6$H$_5$CH$_2$, R$^8$,R$^9$=OCH$_3$)

The reaction was run as in Example 2 using the methoxy dibromide of Example 1 (136 mg., 0.402 mmol), t-butyllithium (0.267 ml, 0.422 mol; 1.58 M in pentane), ether (6 ml), THF (1 ml), 1,2-dimethoxyethane (6 ml) and diethyl(3,5-dimethoxy-4-benzyloxyphenyl)methylene malonate (172 mg., 0.402 mmols.) Workup gave 219 mg of crude product, which was purified by preparative TLC (actone/ether/hexanes, 1/1/3) to give 95 mg of the more polar diastereomer; NMR (CDCl$_3$), δ 7.2–7.5 (5H, multiplet), 6.71 (1H, singlet), 6.42 (1H, singlet), 6.12 (2H, singlet), 5.84 (1H, singlet), 5.80 (1H, singlet), 4.88 (2H, singlet), 4.78 (1H, singlet), 3.44–4.28 (5H, multiplet), 3.62 (6H, singlet), 3.35 (3H, singlet), 2.78 (1H, broad doublet), 2.36 (1H, doublet), 1.10 (6H, two overlapping triplets); and 63 mg of the less polar diastereomer; NMR (CDCl$_3$) δ 7.20–7.52 (5H, multiplet), 6.91 (1H, singlet), 6.40 (1H, singlet), 6.28 (2H, singlet), 5.85 (2H, singlet), 4.91 (2H, singlet), 4.73 (1H, singlet), 3.68–4.50 (5H, multiplet), 3.67 (6H, singlet), 3.52 (3H, singlet), 2.76 (1H, doublet), 2.31 (1H, doublet), 1.13 (6H, two overlapping triplets). Total yield: 158 mg (67%).

EXAMPLE 4

2,2,-Dicarbethoxy-1-(3',4',5'-trimethoxy phenyl)-5,6-methylenedioxyindan (VII-b; where R$^1$ and R$^2$=O—CH$_2$—O—, Z$^1$ and Z$^2$=COOC$_2$H$_5$, R$^7$=CH$_3$, R$^8$, R$^9$=OCH$_3$)

6-bromo-3,4-methylenedioxybenzyl chloride (364 mg, 1.45 mmol) is reacted as in Example 2 with t-butyllithium (0.98 ml, 1.5 mmol, 1.55 M in pentane) and diethyl (3,4,5-trimethoxyphenyl)methylenemalonate (490 mg, 1.45 mmol) to provide the title compound (551 mg, 81% yield).

EXAMPLE 5

2,2-Dicarbethoxy-1-(3',4',5'-trimethoxyphenyl)-6,7-methylenedioxytetralone (III-b; where R$^1$ and R$^2$=O—CH$_2$—O, Z$^1$,Z$^2$=COOC$_2$H$_5$, R$^7$=CH$_3$, R$^8$, R$^9$=OCH$_3$)

To the crude methoxy diester of Example 2 (37 mg) in acetone (1.5 ml) at 0° C. was added 6 N HCl (1.5 ml). After the reaction had been stirred 5 hours at 0° C., TLC (ether/cyclohexane, 1/1) indicated the complete disappearance of the starting material. Jones reagent (20 drops of 2 M, excess) was then added, and the reaction was stirred 40 minutes at 0° C. and quenched with methanol (0.5 ml). The mixture was diluted with water and extracted with methylene chloride. The organic layer was washed with water and saturated sodium chloride, dried over sodium sulfate, and concentrated under reduced pressure to give 28 mg (75%) pure title compound:

m.p. 152.5°–153° C., IR(CHCl$_3$) 1730, 1690 cm$^{-1}$; NMR (CDCl$_3$) δ 7.51 (1H, singlet), 6.65 (1H, singlet) 6.25 (2H, singlet), 6.06 (2H, singlet), 5.08 (1H, singlet), 414 (4H, two overlapping quadruplets), 3.82 (3H, singlet), 3.75 (6H, singlet), 3.25 (2H, singlet), 1.16 (6H, two overlapping triplets); Mass Spec. 500 (M+). Anal: Calculated for C$_{26}$H$_{32}$O$_{10}$: C,62.39; H,5.64. Found: C,62.42; H,5.66.

Although the invention has been described in considerable detail with particular reference to certain preferred embodiments thereof, variations and modifications can be effected within the spirit and scope of the invention as described hereinbefore, and as defined in the appended claims.

What is claimed is:

1. A process for the preparation of a compound of the formula:

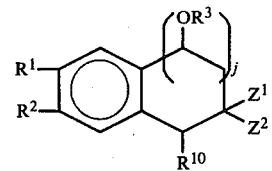

wherein;

R$^1$ represents alkoxy or aralkoxy,

R$^2$ represents hydrogen, alkoxy, aralkoxy, alkyl, or aralkyl, or R$^1$ and R$^2$ taken together represent the group —O—CH$_2$—O—, j is an integer having a value of 0 or 1, R$^3$ represents hydrogen, alkyl, aralkyl, acyl or a protecting group, Z$^1$ represents a non-reacting electron withdrawing group which can be readily converted to a carboxyl group, Z$^2$ represents a non-reacting electron withdrawing group which can be readily converted to a carboxyl group or hydrogen, and R$^{10}$ represents hydrogen, alkyl, aryl, substituted aryl, or aralkyl;

which comprises treating a compound of the formula:

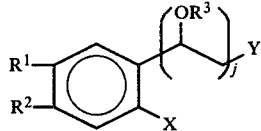

wherein:
R¹, R², R³ and j are as previously defined,
Y represents Cl, Br, I or a leaving group, and
X represents Cl, Br or I;
(A) initially with an alkyl lithium at a temperature of less than −40° C., and
(B) thereafter with a compound of the formula:

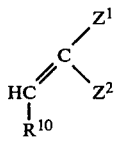

wherein:
Z¹, Z² and R¹⁰ are as previously defined, followed by warming to a temperature of between about 0° C. and about 120° C.

2. The process of claim 1, wherein j has a value of 1.

3. The process of claim 2, wherein said alkyl lithium is a tertiary-alkyl lithium.

4. The process of claim 3, wherein Z¹ represents COOR⁵ and Z² represents COOR⁶ wherein R⁵ and R⁶ are the same or different and represent alkyl or aralkyl.

5. The process of claim 4, wherein R¹⁰ represents a radical of the formula:

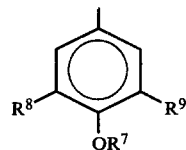

wherein;
R⁷ represents hydrogen, alkyl, aralkyl or acyl, and
R⁸ and R⁹ are the same or different and represent hydrogen, alkyl, aralkyl, alkoxy, aralkoxy, or acyl.

6. The process of claim 5, wherein R³, R⁵ and R⁶ are the same or different and represent lower alkyl.

7. The process of claim 6, wherein R¹ and R² each represent methoxy.

8. The process of claim 6, wherein R¹ and R² taken together represent the group —O—CH₂—O—.

9. The process of claim 8, wherein R⁷ represents methyl and R⁸ and R⁹ each represent methoxy.

10. The process of claim 9, wherein R³ represents methyl and R⁵ and R⁶ each represent ethyl.

11. The process of claim 10 wherein said reaction is initiated at a temperature of less than −78° C. and the reaction mixture is thereafter slowly warmed to a temperature between about 40° C. and 90° C.

12. The process of claim 10 wherein said reaction is initiated at a temperature of about −100° C.

* * * * *

UNITED STATES PATENT AND TRADEMARK OFFICE
CERTIFICATE OF CORRECTION

PATENT NO. : 4,391,982

DATED : July 5, 1983

INVENTOR(S) : Andrew S. Kende et al.

It is certified that error appears in the above—identified patent and that said Letters Patent is hereby corrected as shown below:

In Column 4, the structure at about Line 50 (the structure numbered "(IX)") should read as follows:

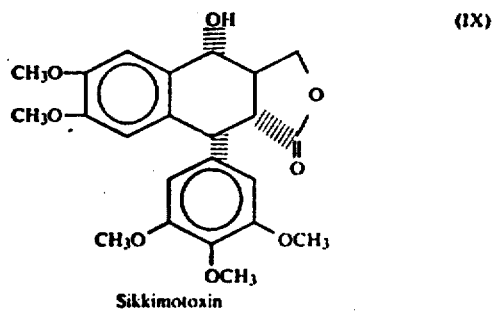

Sikkimotoxin

UNITED STATES PATENT AND TRADEMARK OFFICE
CERTIFICATE OF CORRECTION

PATENT NO. : 4,391,982
DATED : July 5, 1983
INVENTOR(S) : Andrew S. Kende et al.

It is certified that error appears in the above—identified patent and that said Letters Patent is hereby corrected as shown below:

The structure at the top center of the page containing Columns 11 and 12 should read as follows:

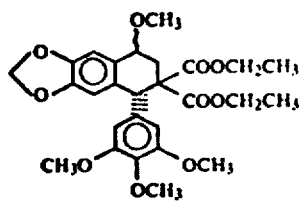

In Claim 12, Line 1, "claim 10" should read -- claim 11 --.

Signed and Sealed this

Twenty-eighth Day of August 1984

[SEAL]

Attest:

GERALD J. MOSSINGHOFF

Attesting Officer    Commissioner of Patents and Trademarks